United States Patent [19]
Field et al.

[11] Patent Number: 5,916,893
[45] Date of Patent: *Jun. 29, 1999

[54] TREATMENT OF A LATENT INFECTION OF HERPES VIRUS

[75] Inventors: Hugh John Field; Alana Maureen Thackray, both of Cambridge; Teresa Helen Bacon, Epsom, all of United Kingdom; David Sutton, Phoenixville, Pa.; Richard Anthony Vere Hodge, Reigate, United Kingdom

[73] Assignee: SmithKline Beecham p.l.c., Brentford, United Kingdom

[ * ] Notice: This patent is subject to a terminal disclaimer.

[21] Appl. No.: 08/845,720

[22] Filed: Apr. 25, 1997

Related U.S. Application Data

[63] Continuation-in-part of application No. 08/522,790, Sep. 1, 1995, Pat. No. 5,840,763.

[30] Foreign Application Priority Data

Dec. 12, 1994 [GB] United Kingdom .................. 9425012
Mar. 31, 1995 [GB] United Kingdom .................. 9506663
Aug. 24, 1995 [GB] United Kingdom .................. 9517308

[51] Int. Cl.$^6$ .................................................. A61K 31/52
[52] U.S. Cl. ........................................... 514/262; 514/934
[58] Field of Search ...................... 514/262, 934

[56] References Cited

U.S. PATENT DOCUMENTS

| | | | |
|---|---|---|---|
| 4,355,032 | 10/1982 | Verheyden et al. | 514/934 |
| 4,423,050 | 12/1983 | Verheyden et al. | 514/934 |
| 4,461,757 | 7/1984 | Ogilvie | 514/934 |

FOREIGN PATENT DOCUMENTS

WO 92/00742  1/1992  WIPO .................. 514/934

OTHER PUBLICATIONS

Boyd et al., Antimicrobial Agents and Chemotherapy, 32(3), pp. 358–363 (1988).

Klein et al., Antimicrobial Agents and Chemotherapy, 27(5), pp. 763–768 (1985).

Klein et al., Antimicrobial Agents and Chemotherapy, 15(5), pp. 723–729 (1979).

Nikkels et al., Drugs, 48(4) pp. 528–548 (1994).

Drugs of the Future, 20(4), pp. 415–417 (1995).

Klein et al., Antimicrobial Agents and Chemotherapy, 24(1), pp. 129–131 (1983).

Field et al., Journal of General Virology, 56(2), pp. 259–265 (1981).

Physicians Gen. Rx., pp. 808–809, 1995.

Drug Facts & Comparisons, pp. 2252–2253, 1990.

*Primary Examiner*—James H. Reamer
*Attorney, Agent, or Firm*—Dara L. Dinner; Stephen Venetianer; Charles Kinzig

[57] ABSTRACT

A method for the treatment of latent infection of herpesviruses in mammals, including humans, which method comprises administering to the mammal in need of such treatment, an effective amount of a compound of formula (A):

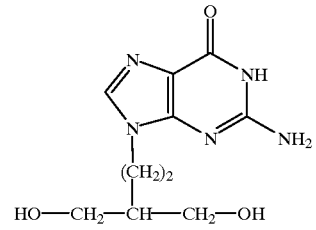

(A)

or a bioprecursor, or a pharmaceutically acceptable salt, phosphate ester and/or acyl derivative of either of the foregoing.

15 Claims, No Drawings

TREATMENT OF A LATENT INFECTION OF HERPES VIRUS

This is a continuation-in-part of application Ser. No. 08/522,790, filed on Sep. 1, 1995, now U.S. Pat. No. 5,840,763.

This invention relates to treatment of latent infection of herpesviruses.

When used herein, 'treatment' includes prophylaxis as appropriate.

EP-A-141927 (Beecham Group p.l.c.) discloses penciclovir, the compound of formula (A):

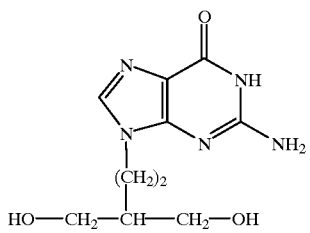

(A)

and salts, phosphate esters and acyl derivatives thereof, as antiviral agents. The sodium salt hydrate of penciclovir is disclosed in EP-A-216459 (Beecham Group p.l.c.). Penciclovir and its antiviral activity is also disclosed in Abstract P.V11-5 p.193 of 'Abstracts of 14th Int. Congress of Microbiology', Manchester, England 7–13 Sep.1986 (Boyd et. al.).

Orally active bioprecursors of the compound of formula (A) are of formula (B):

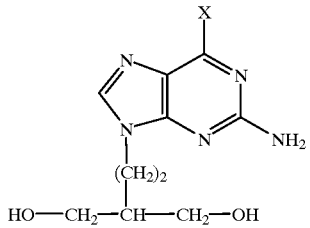

(B)

and salts and derivatives thereof as defined under formula (A); wherein X is $C_{1-6}$ alkoxy, $NH_2$ or hydrogen. The compounds of formula (B) wherein X is $C_{1-6}$ alkoxy or $NH_2$ are disclosed in EP-A-141927 and the compounds of formula (B) wherein X is hydrogen, disclosed in EP-A-182024 (Beecham Group p.l.c.) are preferred prodrugs. A particularly preferred example of a compound of formula (B) is that wherein X is hydrogen and wherein the two OH groups are in the form of the acetyl derivative, described in Example 2 of EP-A-182024, hereinafter referred to as famciclovir.

The compounds of formulae (A) and (B) and salts and derivatives thereof have been described as useful in the treatment of infections caused by herpesviruses, such as herpes simplex type 1 and herpes simplex type 2.

Previous work has shown that if antiviral treatment is delayed beyond a few hours after infection then latency is established. Once a latent infection is established, the infection can recurr.

It has now been shown in mice that famciclovir treatment can prevent the establishment of competent latency when treatment is commenced 18 h (first experiment) and up to 4 days (second experiment) after infection. It has also now been shown that latency can be prevented in an experiment in immunocompromised mice. The potential clinical advantage is that a patient, within 4 days of contact, may be treated with famciclovir to prevent not only the acute infection but also the development of latency and so avoid recurrences. Furthermore, it is thought that there may be a slow natural loss of latently infected cells and recurrent infections may be required in order to maintain the burden of latently infected cells by establishing latency in new cells. Therefore, suppressive treatment with famciclovir over a prolonged period (up to several years) may prevent new cells becoming latently infected. The result would then be curative treatment, the patient having no recurrences thereafter.

Accordingly, the present invention provides a method of treatment of latent infection of herpesviruses in humans, which method comprises the administration to the human in need of such treatment, an effective amount of a compound of formula (A):

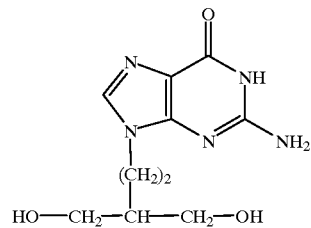

(A)

or a bioprecursor, or a pharmaceutically acceptable salt, phosphate ester and/or acyl derivative of either of the foregoing.

The term 'acyl derivative' is used herein to include any derivative of the compounds of formula (A) in which one or more acyl groups are present. Such derivatives are included as bioprecursors of the compounds of formula (A) in addition to those derivatives which are per se biologically active.

The compound of formula (A) may be in one of the forms disclosed in EP-A-216459 (Beecham Group p.l.c.).

Examples of bioprecursors, pharmaceutically acceptable salts and derivatives are as described in the aforementioned European Patent references, the subject matter of which are incorporated herein by reference.

A particular compound of formula (B) of interest is 9-(4-acetoxy-3-acetoxymethylbut-1-yl)-2-aminopurine, known as famciclovir (FCV), the well-absorbed oral form of penciclovir (PCV).

The compound of formula (A), bioprecursors, salts and derivatives may be prepared as described in the aforementioned European Patent references.

The compound, in particular, famciclovir, may be administered by the oral route to humans and may be compounded in the form of syrup, tablets or capsule. When in the form of a tablet, any pharmaceutical carrier suitable for formulating such solid compositions may be used, for example magnesium stearate, starch, lactose, glucose, rice, flour and chalk. The compound may also be in the form of an ingestible capsule, for example of gelatin, to contain the compound, or in the form of a syrup, a solution or a suspension. Suitable liquid pharmaceutical carriers include ethyl alcohol, glycerine, saline and water to which flavouring or colouring agents may be added to form syrups. Sustained release formulations, for example tablets containing an enteric coating, are also envisaged.

For parenteral administration, fluid unit dose forms are prepared containing the compound and a sterile vehicle. The compound depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

Preferred parenteral formulations include aqueous formulations using sterile water or normal saline, at a pH of around 7.4 or greater, in particular, containing penciclovir sodium salt hydrate.

As is common practice, the compositions will usually be accompanied by written or printed directions for use in the medical treatment concerned.

A suitable dosage unit might contain from 50 mg to 1 g of active ingredient, for example 100 to 500 mg. Such doses may be administered 1 to 4 times a day or more usually 2 or 3 times a day. The effective dose of compound will, in general, be in the range of from 0.2 to 40 mg per kilogram of body weight per day or, more usually, 10 to 20 mg/kg per day. in the case of famciclovir, the dosage unit would be 125 mg, 250 mg, 500 mg or 750 mg, preferably 125 mg or 250 mg.

For prevention of establishment of competent latency, the treatment is preferably carried out as soon as possible after contact with the virus, preferably within 18 hours, although up to five days or possibly longer is acceptable. The treatment period is usually 3 to 14 days, more usually 5 to 10 days, often 5 or 7 days.

For treatment of established recurrent disease, the treatment period is up to 5 years, for example, up to 1, 2, 3, 4, and 5 years.

The present invention also provides the use of a compound of formula (A) or a bioprecursor, or a pharmaceutically acceptable salt, phosphate ester and/or acyl derivative of either of the foregoing, in the preparation of a medicament for use in the treatment of latent infection of herpesviruses. Such treatment may be carried out in the manner as hereinbefore described.

The present invention further provides a pharmaceutical composition for use in the treatment of latent infection of herpesviruses, which comprises an effective amount of a compound of formula (A) or a bioprecursor, or a pharmaceutically acceptable salt, phosphate ester and/or acyl derivative of either of the foregoing, and a pharmaceutically acceptable carrier. Such compositions may be prepared in the manner as hereinafter described.

The compound of formula (A) and its prodrugs show a synergistic antiviral effect in conjunction with interferons; and treatment using combination products comprising these two components for sequential or concomitant administration, by the same or different routes, are therefore within the ambit of the present invention. Such products are described in EP-A-271270 (Beecham Group p.l.c.).

The following results from animal studies illustrate the invention.

EXPERIMENTS IN MICE INFECTED WITH HSV-1 VIRUS

A cutaneous infection was established by inoculation of the ear pinnae of mice with HSV-1 (SC16) and the effects of oral famciclovir on the latent virus infection was investigated.

BALB/c female mice (Bantin and Kingman, Kingston, Hull, UK) were purchased at 3 to 4 weeks old and inoculated one week later. Virus suspension (10 ul) containing $5 \times 10^4$ p.f.u. were inoculated into the skin of the left ear pinna. Skin thickness was measured daily in individual mice by means of an Engineers' micrometre screw gauge. (ref. Nash et al, 1980, J. Gen. Virol. 48, 351–357). These mice were kept for 3 (Experiment 1) or 4 (Experiment 2) months and then killled. The trigeminal ganglia and cervical dorsal root ganglia were removed and co-cultivated. Those cultures showing virus replication were recorded as positive.

Experiment 1

In a first experiment, mice were treated within 18h and treatment ceased on day 10 post infection.

Of the 24 untreated control mice, 12 showed latent infection in the trigeminal ganglia (TG) and 20 showed latent infection in the cervical dorsal route ganglia (DRG). All 24 control mice showed either TG or DRG latency. None of the FCV treated mice showed any latency.

Experiment 2

In a second experiment, antiviral treatment was initiated on days 1, 2, 3, 4 or 5 post-infection (p.i.) and and ceased on day 10 p.i.. The compounds were administered ad libitum in the drinking water, at 1 mg/ml (approximately 100 mg/kg/day).

The results are as shown in the following table:

Note: The groups 1 and 2 received the same treatment regimens but the results ere assayed separately.)

| Antiviral Therapy | Latency (Group 1) | | | | Latency (Group 2) | | | | Latency Total % Mice with virus + ve ganglia on day 120 (n = 16) | Acute Total % Mice with virus + ve ganglia on day 8 (n = 8) |
|---|---|---|---|---|---|---|---|---|---|---|
| | TG + ve/8 | | DRG + ve/8 | | TG + ve/8 | | DRG + ve/8 | | | |
| (days) | Lt | Rt | Lt | Rt | Lt | Rt | Lt | Rt | L/RTG + DRG | L/RTG + DRG |
| None | 8 | 4 | 8 | 5 | 8 | 6 | 8 | 2 | 100 | 100 |
| 5–10 | 4 | 0 | 4 | 0 | 2 | 0 | 2 | 0 | 38 | 100 |
| 4–10 | 2 | 0 | 2 | 0 | 0 | 0 | 0 | 0 | 13 | 100 |
| 3–10 | 0 | 0 | 0 | 0 | 0 | 0 | 0 | 0 | 0 | 0 |
| 2–10 | 0 | 0 | 0 | 0 | 0 | 0 | 0 | 0 | 0 | 0 |
| 1–10 | 0 | 0 | 0 | 0 | 0 | 0 | 0 | 0 | 0 | 0 |

Four months later, latent virus could be reactivated in ganglia explants (ipsilateral and contralateral trigeminal and dorsal root) from all of 16 control mice. Latent virus was not reactivated from the ganglia of FCV-treated mice, except ipsilateral ganglia, and only when the start of therapy was delayed until days 4 p.i. (2/16) or 5 p.i (6/16).

Similar results were obtained when compounds were administered twice daily by gavage at 50 mg/kg per dose.
Experiment 3

Mice were immunosupressed with Cyclosporin A (CyA) from day -2 to day =10 (day 0 being the day of infection). Groups of mice were untreated (control), or treated with famciclovir orally at 50 mg/kg twice daily from 22 h after infection to 5.5 or 10.5 days. The ganglia were examined for reactivation of infectious virus 1 or 4 months later and the results are shown in the Table below.

|  | LTG (n = 6) | RTG (n = 6) | LDR (n = 6) | RDR (n = 6) |
|---|---|---|---|---|
| Control | 6 | 4 | 6 | 3 |
| FCV | 0 | 0 | 0 | 0 |

TG = trigeminal DRG = dorsal root ganglia L/R = left/right

EXPERIMENTS IN MICE INFECTED WITH HSV-2 VIRUS

A cutaneous infection was established by inoculation of the ear pinnae of mice with HSV-2 (Bry) and the effects of oral famciclovir on the latent virus infection was investigated. Treatment was 50 mg/kg twice daily for 5 days starting 22 h post-infection.

The table shows the number of mice/group with positive latent infection in the trigeminal or cervical dorsal root ganglia.

| Group | No. of mice with +ve ganglia mice/ number of mice tested ganglion | | | | % yielding at least one +ve |
|---|---|---|---|---|---|
|  | Left T/G | Right T/G | Left CDR | Right CDR |  |
| Control | 10/10 | 10/10 | 10/10 | 6/10 | 100 |
| famciclovir | 0/10 | 0/10 | 0/10 | 0/10 | 0 |

T/G = trigeminal CRG = Cervical dorsal root ganglia

Evidence from a murine immunosuppression model that famciclovir is effective against an on-going chronic herpes simplex virus infection.

Immunosuppression was induced in mice by means of cyclosporin administered on alternate days. When such mice were inoculated in the ear pinna with HSV-1, a chronic infection was established. Virus replication continued in both skin and central nervous system for 20 days, the duration of the experiment. During this time, clinical signs including inflammation of the ear, weight loss and cumulative mortality were monitored. Famciclovir or valaciclovir (50 mg/kg b.i.d). was commenced 5 days after virus inoculation for a period of 5 days. Famciclovir prevented mortality (which in untreated mice reached 50% by day 20). Furthermore, weight gain was restored to uninfected control levels within 3 days of starting treatment and inflammation (as judged by skin thickness) returned to normal levels within 4 days. Virus titres were measured daily throughout the experiment. Infectious virus was cleared from both skin and neural tissues (representing a reduction in approx. 4 log 10 p.f.u./organ) and, following cessation of famciclovir therapy, there was no recurrence of infectious virus despite the continuation of immunosuppression for a further 10 days. In, recurrence of virus replication on several days was observed in mice that had been treated with valaciclovir in both skin and brainstem. It was of interest that in a separate group of mice that were infected without immunosuppression, recurrence on cessation of valaciclovir still occurred, but only in brainstem and not in the ear pinna. Our results provide further evidence of the potent antiviral activity of famciclovir in a relevant animal model for chronic herpes simplex infection.

Further investigation into the recurrence of infectious virus in the nervous system of mice infected with HSV-1 on cessation of valaciclovir therapy.

Previously we have reported the contrasting effects of famciclovir and valaciclovir in murine infections models for HSV- 1 and HSV-2. A striking result was the reproducible recurrence of infectious virus in the nervous system of mice following cessation of valaciclovir therapy for 5 or 10 days while no such recurrence was observed after famciclovir therapy (J. Inf. Dis. 73, 291–299 & Antimicrob. Ag. Chemother. 40(4) in press). We had noted a recurrence of viral replication with aciclovir (ip, once daily) (Field et al, 1979, Antimicrob. Ag. Chemother. 15:554–561). We therefore compared aciclovir with its prodrug, valaciclovir. Mice were infected with HSV- 1 in the skin of the ear. Valaciclovir was administered as before (50 mg/Kg b.i.d. from day 1 to 5 post infection). Further groups of mice were treated with aciclovir (50 mg/Kg b.i.d, ip.) or aciclovir ad. lib. in the drinking water (approx. 160 mg/Kg/day). The clinical signs were noted and mortality, weight-gain/loss, inflammation in the ear were measured daily. Virus replication in the skin of the ear and in brain stem and trigeminal ganglion was measured daily from day 1 to 14 post infection. Aciclovir i.p. was the most, and valaciclovir the least, effective of the three regimens. When treatment was terminated on day 5; recurrence of infectious virus was observed in brain stem on day 8 in mice that had been treated with aciclovir in drinking water and on day 9 in mice that had been given valaciclovir. Recurrence in trigeminal ganglia was seen on day 8 but only in mice that had been given valaciclovir. No recurrences of infectious virus were recorded in the skin of the ear. These results confirm that, in contrast to famciclovir, neither oral aciclovir or valaciclovir therapy prevents virus recurrence, a factor which may limit their antiviral efficacy in man.

What we claim is:

1. A method for the treatment of a latent infection of herpes viruses in a human in need thereof which method comprises administering to said human an effective amount of a compound of formula (A):

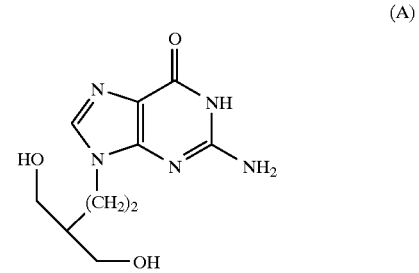

(A)

or a bioprecurser, or a pharmaceutically acceptable salt, phosphate ester and/or acyl derivative or either of the foregoing at greater than 18 hours post-infection.

2. A method according to claim 1 wherein the treatment is for latent infection of herpes simplex type 1 infection.

3. A method according to claim 1 wherein the treatment is for latent infection of herpes simplex type 2 infection.

4. A method according to claim 1 wherein the Compound is famciclovir.

5. A method according to claim 4 wherein famciclovir is administered at a dose of 125 mg, 250 mg, 500 mg, 750 mg, or 1 g, once, twice or three times a day.

6. The method according to claim 1 wherein the time of administration is four (4) days or greater post-infection.

7. The method according to claim 1 wherein the length of time for reduction of or reactivation of the latent herpes viruses is from 3 to 14 days.

8. The method according to claim 1 wherein the compound of Formula (A) is penciclovir, or a pharmaceutically acceptable salt thereof.

9. A method for the reduction, or prevention of a herpes virus becoming latent and subsequently reactivating in a human in need thereof, which method comprises administering to said human an effective amount of famciclovir or penciclovir, or a pharmaceutically acceptable salt thereof, at greater than 18 hours post-infection.

10. The method according to claim 9 wherein the latent herpes viral infection is HSV-1.

11. The method according to claim 9 wherein the latent herpes viral infection is HSV-2.

12. The method according to claim 9 wherein famciclovir is administered at a dose of 125 mg, 250 mg, 500 mg, 750 mg, or 1 gram.

13. The method according to claim 12 wherein the dose is administered once, twice or three times a day.

14. The method according to claim 9 wherein the time of administration is four (4) days or greater post-infection.

15. The method according to claim 9 wherein the length of time for reduction of or reactivation of the latent herpes viruses is from 3 to 14 days.

* * * * *